US00PP19228P2

(12) United States Plant Patent
Aoki

(10) Patent No.: US PP19,228 P2
(45) Date of Patent: Sep. 16, 2008

(54) *HIBISCUS* PLANT NAMED 'HAIGHT ASHBURY'

(50) Latin Name: *Hibiscus acetosella*
Varietal Denomination: Haight Ashbury

(75) Inventor: Kerrie Aoki, Oceanside, CA (US)

(73) Assignee: Amerinova Properties, LLC, Bonsall, CA (US)

( * ) Notice: Subject to any disclaimer, the term of this patent is extended or adjusted under 35 U.S.C. 154(b) by 0 days.

(21) Appl. No.: 11/801,680

(22) Filed: May 9, 2007

(51) Int. Cl.
*A01H 5/00* (2006.01)

(52) U.S. Cl. ..... Plt./257
(58) Field of Classification Search ..... Plt./257
See application file for complete search history.

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of *Hibiscus* plant named 'Haight Ashbury', characterized by its upright and somewhat outwardly spreading plant habit; freely branching habit; and maple leaf-shaped leaves that are green, greyed red, greyed purple and greyed orange in color.

1 Drawing Sheet

Botanical designation: *Hibiscus acetosella.*
Cultivar denomination: 'HAIGHT ASHBURY'.

BACKGROUND OF THE INVENTION

The present invention relates to a new and distinct cultivar of *Hibiscus,* botanically known as *Hibiscus acetosella,* and hereinafter referred to by the name 'Haight Ashbury'.

The new *Hibiscus* is a naturally-occurring branch mutation of the *Hibiscus acetosella* cultivar Maple Sugar, disclosed in U.S. Plant Pat. No. 16,286. The new *Hibiscus* was discovered and selected by the Inventor in a controlled environment in Bonsall, Calif. in 2005.

Asexual reproduction of the new *Hibiscus* by vegetative cuttings in a controlled environment in Bonsall, Calif. since 2005, has shown that the unique features of this new *Hibiscus* are stable and reproduced true to type in successive generations.

SUMMARY OF THE INVENTION

The cultivar Haight Ashbury has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Haight Ashbury'. These characteristics in combination distinguish 'Haight Ashbury' as a new and distinct cultivar of *Hibiscus:*

1. Upright and somewhat outwardly spreading plant habit.
2. Freely branching habit.
3. Maple leaf-shaped leaves the are green, greyed-red, greyed purple and greyed orange in color.

Plants of the new *Hibiscus* can be compared to plants of the parent, the cultivar Maple Sugar. Plants of the new *Hibiscus* differ primarily from plants of the cultivar Maple Sugar in leaf color as plants of the cultivar Maple Sugar have burgundy-colored leaves.

Plants of the new *Hibiscus* can be compared to plants of the *Hibiscus acetosella* cultivar Panama Red, not patented. Plants of the new *Hibiscus* differ primarily from plants of the cultivar Panama Red in leaf color as plants of the cultivar Panama Red have dark burgundy-colored leaves.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph at the bottom of the sheet comprises a side perspective view of three typical plants of 'Haight Ashbury' grown in a container.

The photograph at the top of the sheet is a close-up view of typical leaves of 'Haight Ashbury'.

DETAILED BOTANICAL DESCRIPTION

The aforementioned photographs and following observations, measurements and values describe plants grown in Bonsall, Calif. in containers during the winter and early spring in polyethylene-covered greenhouses under conditions which closely approximate commercial production. During the production of the plants, day temperatures ranged from about 18° C. to about 30° C. and night temperatures ranged from about 12° C. to about 18° C. Plants were about three months old when the photographs and the description were taken. In the description, color references are made to The Royal Horticultural Society Colour Chart, 1995 Edition, except where general terms of ordinary dictionary significance are used.

Botanical classification: *Hibiscus acetosella* cultivar Haight Ashbury.

Parentage: Naturally-occurring branch mutation of the *Hibiscus acetosella* cultivar Maple Sugar, disclosed in U.S. Plant Pat. No. 16,286.

Propagation:

*Type.*—By vegetative terminal cuttings.

*Time to initiate roots, summer.*—About 10 days at 35° C.

*Time to initiate roots, winter.*—About 15 days at 25° C.

*Time to develop roots, summer.*—About 35 days at 35° C.

*Time to develop roots, winter.*—About 45 days at 25° C.

*Root description.*—Fibrous; white in color.

*Rooting habit.*—Freely branching; moderately dense.

Plant description:

*Plant form and growth habit.*—Upright and somewhat outwardly spreading plant habit. Moderately vigorous growth habit.

*Branching habit.*—Freely branching, usually about seven lateral branches develop after pinching (removal of terminal apex).

*Plant height.*—About 30 cm.

*Plant diameter* (*area of spread*).—About 24 cm to 30 cm.

Lateral branch description:

*Length.*—About 26 cm.

*Diameter.*—About 6 mm.

*Internode length.*—About 2.5 cm.

*Texture, immature.*—Smooth, glabrous.

*Texture, mature.*—Sparsely pubescent.

*Color.*—183A to 183B.

Foliage description:

*Arrangement.*—Alternate, single.

*Length.*—About 6.2 cm.

*Width.*—About 6.5 cm.

*Shape.*—Maple leaf-shape; three to five lobes with deep sinuses.

*Apex.*—Acute to slightly acuminate.

*Base.*—Obtuse.

*Margin.*—Irregularly serrate.

*Texture, upper and lower surfaces.*—Smooth, glabrous.

*Venation pattern.*—Palmate.

*Color.*—Developing foliage, upper surface: 183A to 183C. Developing foliage, lower surface: 187A to 187B. Mature foliage, upper surface: Random and irregular sectors of 147A , 147B, 146B to 146C, 182C, 186B to 186C, 165C and 164D; venation, 185A. Mature foliage, lower surface: Random and irregular sectors of 182B and 197A to 197B; venation, 184A to 184B.

*Petiole.*—Length: About 4.8 cm. Diameter: About 2 mm. Texture, upper surface: Pubescent. Texture, lower surface: Smooth, glabrous. Color, upper and lower surfaces: 184B.

Flower description: Flower development has not been observed on plants of the new *Hibiscus.*

Temperature tolerance: Plants of the new *Hibiscus* have been observed to tolerate temperatures from about 5° C. to about 35° C.

Pathogen/pest resistance: Plants of the new *Hibiscus* have not been shown to be resistant to pathogens and pests common to *Hibiscus.*

It is claimed:

1. A new and distinct *Hibiscus* plant named 'Haight Ashbury' as illustrated and described.

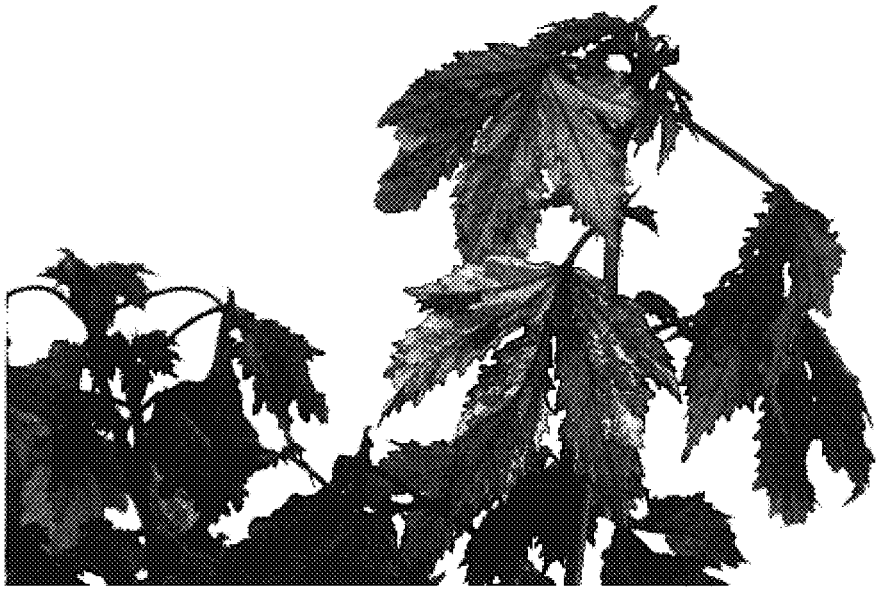
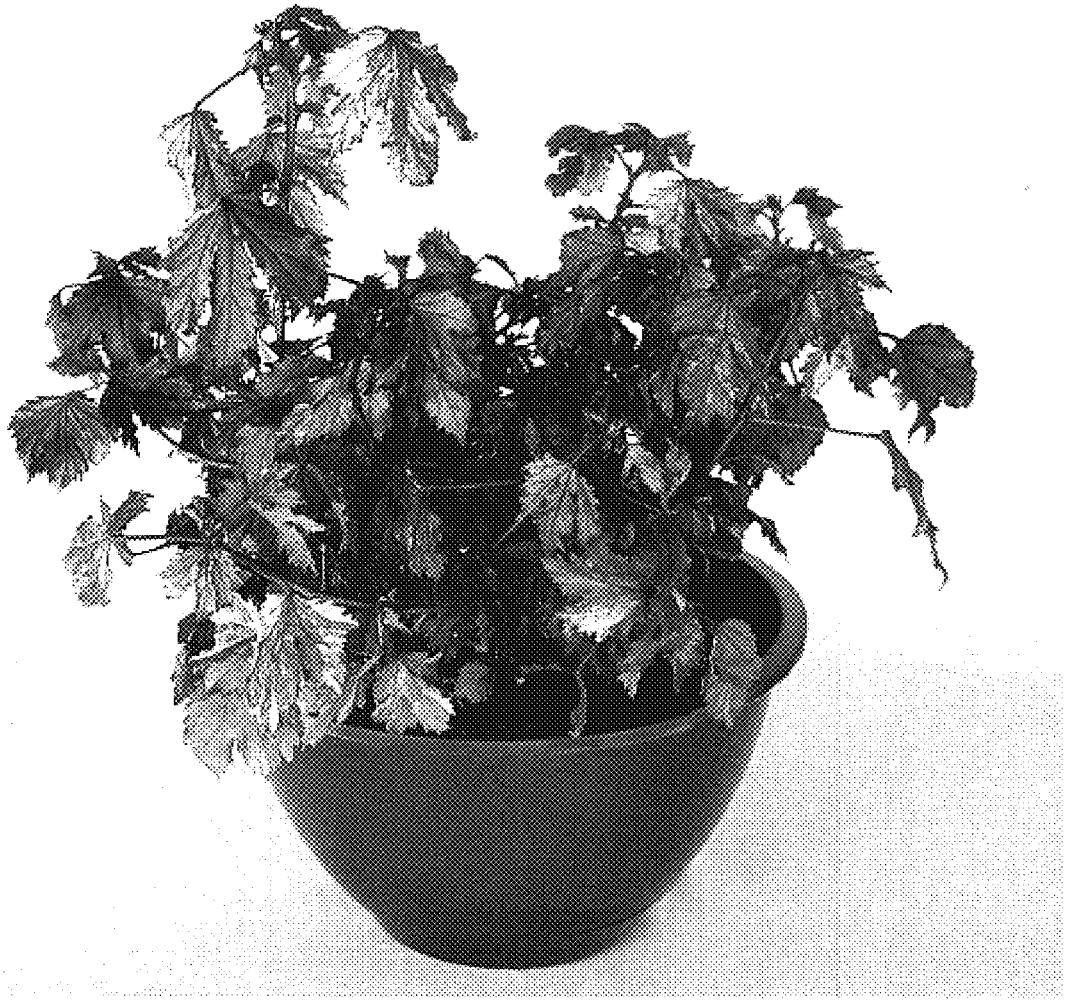

* * * * *